US008623392B2

(12) United States Patent
Morino et al.

(10) Patent No.: US 8,623,392 B2
(45) Date of Patent: Jan. 7, 2014

(54) ALLERGEN INACTIVATING AGENT

(75) Inventors: Hirofumi Morino, Akashi (JP); Takashi Shibata, Suita (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 255 days.

(21) Appl. No.: 12/530,396

(22) PCT Filed: Feb. 15, 2008

(86) PCT No.: PCT/JP2008/052497

§ 371 (c)(1),
(2), (4) Date: Nov. 24, 2009

(87) PCT Pub. No.: WO2008/114553

PCT Pub. Date: Sep. 25, 2008

(65) Prior Publication Data

US 2010/0062074 A1 Mar. 11, 2010

(30) Foreign Application Priority Data

Mar. 22, 2007 (JP) ................................ 2007-074993
May 21, 2007 (JP) ................................ 2007-134404
Oct. 31, 2007 (JP) ................................ 2007-283627

(51) Int. Cl.

| | |
|---|---|
| ***A01N 59/08*** | (2006.01) |
| *A61K 33/14* | (2006.01) |
| *A61K 33/40* | (2006.01) |
| *A01N 25/32* | (2006.01) |
| *A01N 39/00* | (2006.01) |
| *C01B 3/00* | (2006.01) |
| *C01B 11/02* | (2006.01) |
| *C02F 1/70* | (2006.01) |
| *C06B 23/00* | (2006.01) |
| *C06B 43/00* | (2006.01) |
| *C09B 3/00* | (2006.01) |

(52) U.S. Cl.
USPC ........... 424/406; 424/613; 424/661; 423/477; 252/188.1; 252/188.28

(58) Field of Classification Search
USPC ........ 424/661, 406, 613; 423/477; 252/188.1, 252/188.28
See application file for complete search history.

(56) References Cited

U.S. PATENT DOCUMENTS 5,019,402 A * 5/1991 Kross et al. .................. 424/665
5,622,725 A * 4/1997 Kross ............................ 424/665

(Continued)

FOREIGN PATENT DOCUMENTS

EP 2 130 794 A1 12/2009
JP 04-281821 A 10/1992

(Continued)

OTHER PUBLICATIONS

Kathleen S. Failla, "A Veteran Compound That May Treat Feed and AIDS", May 5, 1985, Chemical Week; vol. 136, No. 18, p. 29 (Abstract only).*

(Continued)

*Primary Examiner* — Jane C Oswecki
(74) *Attorney, Agent, or Firm* — Buchanan Ingersoll & Rooney PC

(57) ABSTRACT

An allergen inactivating agent for preventing allergic manifestations or alleviating symptoms by reducing antigenicity of an allergen through contact with the allergen includes dissolved chlorine dioxide as an active ingredient.

4 Claims, 7 Drawing Sheets

(56) References Cited

U.S. PATENT DOCUMENTS

| | | | | |
|---|---|---|---|---|
| 6,196,156 | B1 * | 3/2001 | Denesuk et al. | 119/28.5 |
| 6,200,557 | B1 | 3/2001 | Ratcliff | |
| 6,231,830 | B1 | 5/2001 | Madray | |
| 2004/0071788 | A1 | 4/2004 | Fuhr | |
| 2006/0045855 | A1 | 3/2006 | Sasson | |
| 2007/0196357 | A1 * | 8/2007 | Alimi et al. | 424/114 |
| 2009/0053325 | A1 * | 2/2009 | Ogata | 424/661 |

FOREIGN PATENT DOCUMENTS

| | | | |
|---|---|---|---|
| JP | 06-247814 | | 9/1994 |
| JP | 11-278808 | A | 10/1999 |
| JP | 2000-063217 | A | 2/2000 |
| JP | 2004-089673 | | 3/2004 |
| JP | 2006-149900 | A | 6/2006 |
| WO | WO 03/082304 | A1 | 10/2003 |
| WO | WO2005/065383 | * | 7/2005 |
| WO | WO 2005/065383 | A2 | 7/2005 |
| WO | WO 2006/039565 | A2 | 4/2006 |
| WO | WO 2007/061092 | A1 | 5/2007 |

OTHER PUBLICATIONS

S C Wilson et al., "Effect of chlorine dioxide gas on fungi and mycotoxins associated with sick building syndrome", 2005, Applied and Environmental Microbiology, vol. 71, No. 9, pp. 5399-5403 (Abstract only).*

Qi-huan HE et al., Study of chlorine dioxide existence form in stabilized chlorine dioxide solution, 2001, Industrial Water Treatment, 21(4): 6-8. Abstract and Translation of PCT108-016-CN, Paragraphs 1 (Theoretical analysis); 4 (Conclusions); and 2 (Reference Document 2), supplied by Applicants.*

Qi-huan HE et al., Industrial Waste Treatment, 2001, 21(4): 8-10.*

Reference Document 2 of Qi-huan HE et al., Industrial Waste Treatment, 2001, 21(4): 8-10; attachment to CN 10004, PCT108-016-CN; partial translation only.*

He et al., "Study of chlorine dioxide existence form in stabilized chlorine dioxide solution," Apr. 2001, Industrial Waste Treatment, 21(4): 8-10.*

International Search Report issued by Japanese Patent Office as International Searching Authority in International Application No. PCT/JP2008/052497, dated May 13, 2008.

Jun Wen Li et al., "Mechanisms of Inactivation of Hepatitis A Virus in Water by Chlorine Dioxide", Water Research, 2004 (month unknown), vol. 38, pp. 1514-1519.

Elizabeth Matsui et al., "Allergic Potency of Recombinant FIL d 1 Is Reduced by Low Concentrations of Chlorine Bleach", The Journal of Allergy and Clinical Immunology, Feb. 2003, vol. 111, No. 2, pp. 296-401.

John W. Martyny et al, "Aerosolized Sodium Hypochlorite Inhibits Viaility and Allergenicity of Mold on Building Materials", The Journal of Allergy and Clinical Immunology, Aug. 2005, vol. 116, No. 3, pp. 630-635.

Yoko Akimoto et al., "360—Denkaisui Ni Yoru Sugi Kafun Allergen Fukatsuka Ni Kansuru Kento" (Study of Cedar Pollen Allergen Inactivation by Elecrolyzed Water), Japanese Journal of Allergology, 2004 (month unknown), vol. 53, No. 8/9, p. 970 (with English language translation).

English Language Translation of International Preliminary Report on Patentability and Written Opinon issued on Sep. 22, 2009, by the International Bureau of WIPO.

Chinese Office Action issued Sep. 26, 2011 by the Chinese Patent Office in corresponding Chinese Patent Application, and partial English translation of the Chinese Office Action.

Qi-huan HE et al., "Study of chlorine dioxide existence form in stabilized chlorine dioxide solution", *Industrial Waste Treatment*, Apr. 2001, vol. 21, No. 4, pp. 8-10, and partial English language translation.

Official Action (Extended European search report) dated Jan. 23, 2012, issued in corresponding European Application No. 08711327.0.

Office Action dated Oct. 22, 2012, issued in corresponding European Application No. 08711327.0.

Chinese Office Action issued Sep. 26, 2011 by the Chinese Patent Office in corresponding Chinese Patent Application, and English translation of the Chinese Office Action.

Qi-huan HE et al., "Study of chlorine dioxide existence form in stabilized chlorine dioxide solution," *Industrial Water Treatment*, Apr. 2001, vol. 21, No. 4, pp. 8-10, and English language translation.

* cited by examiner

ALLERGEN INACTIVATING AGENT

TECHNICAL FIELD

The present invention relates to an allergen inactivating agent (hereinbelow, frequently and simply referred to as "inactivating agent"). Particularly, the present invention relates to an allergen inactivating agent for preventing allergic manifestations and alleviating allergic symptoms by reducing antigenicity of an allergen through contact with the allergen.

BACKGROUND ART

As is well known, a substance that is a factor for causing an allergic symptom is called allergen or antigen. Pollen and house dust, such as mold, mold spore, mite body, and mite feces, can be mentioned as allergen. Normally, an immunologic reaction (self-defense reaction) works advantageously for protecting the human body from these foreign substances, but allergic symptom is resulted when the immunologic reaction works disadvantageously. When leading a stressful life, i.e., becoming extremely nervous in social and daily lives, one could gradually disrupt the function of autonomic nerves and lose hormonal balance. This is believed to be a state in which allergy is likely to manifest. In addition, as another factor which is likely to cause an allergic symptom, there can be mentioned a closed living environment in which an amount of house dust as a predominant allergen is increased.

For the measurements against allergy (such as pollen allergy) to this day, the exposure to pollen has been suppressed to minimum, by using a mask or goggle with high sealing effect for blocking pollen or a dust collector or air purification device for removing pollen. When allergic symptom is manifested, nose or eyes has been washed, and therapeutic medicine for alleviating a symptom has been administered. Use of therapeutic medicine is merely a temporal suppression of the symptom, and it should be administered every time the symptom appears, and thus there is concern that a side effect might occur.

Recently, as a method for preventing pollen allergy, there has been proposed a method in which the pollen allergy allergen is treated with alkali, acid and protease under heated conditions (see Patent Document 1).

Patent Document 1: Japanese Patent Application JP2004-89673A

SUMMARY

The present inventors made intensive and extensive studies with the view towards preventing allergic manifestations and alleviating allergic symptoms, by inactivating the allergen itself, or reducing the antigenicity of the allergen. As a result, they discovered that chlorine dioxide reduces the antigenicity of the allergen, and completed the present invention.

In a first aspect of the present invention, there is provided an allergen inactivating agent for preventing allergic manifestations or alleviating symptoms by reducing antigenicity of an allergen through contact with the allergen, which includes chlorine dioxide as an active ingredient.

In a second aspect of the present invention, in the allergen inactivating agent, the chlorine dioxide is a chlorine dioxide solution in which chlorine dioxide is dissolved in water.

In a third aspect of the present invention, in the allergen inactivating agent, the chlorine dioxide is chlorine dioxide gas.

In a fourth aspect of the present invention, in the allergen inactivating agent, the allergen is a pollen allergy allergen.

In a fifth aspect of the present invention, in the allergen inactivating agent, the allergen is a mite allergen.

In a sixth aspect of the present invention, in the allergen inactivating agent, the allergen is a fungal allergen.

According to the present invention, the allergen inactivating agent inactivates the allergen itself or reduces the antigenicity of the allergen, and thus can prevent allergic manifestations and alleviate allergic symptoms, which may otherwise be caused by pollen, house dust or the like.

DETAILED DESCRIPTION

Figure 1:
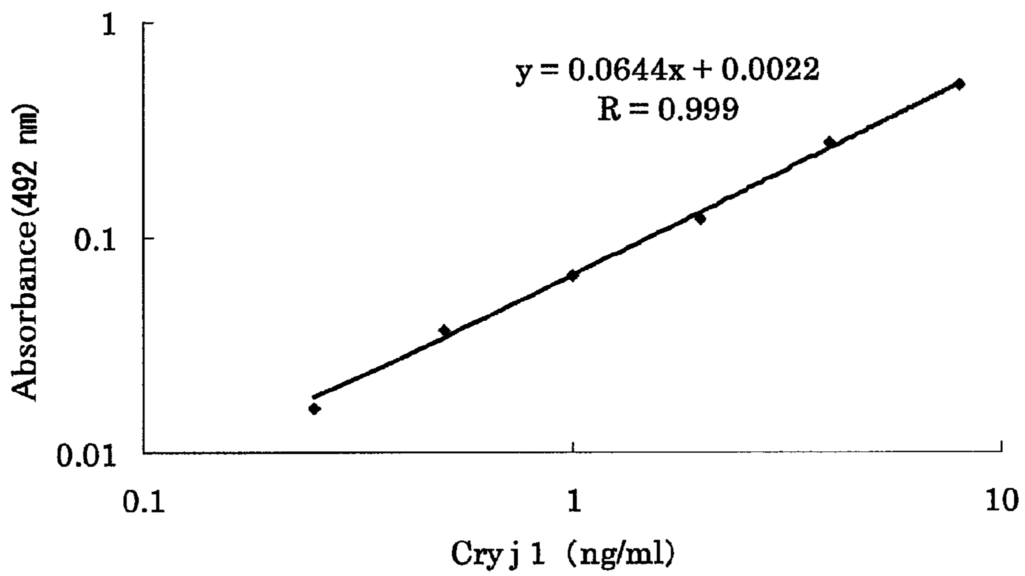
FIG. 1 is a graph showing a standard curve for Cry j1.

An embodiment of the present invention will be described below, but the present invention should not be limited to this embodiment.

The present invention is an allergen inactivating agent for preventing allergic manifestations or alleviating symptoms by reducing antigenicity of an allergen through contact with the allergen, which includes chlorine dioxide as an active ingredient.

Allergen

Examples of the allergen to be treated with the inactivating agent of the present invention include those of cedar pollen (e.g., Cry j1, Cry j2), Japanese cypress pollen (e.g., Cha o1, Cha o2), ragweed pollen (e.g., Amb a1), buckwheat pollen, and house dust (such as mold, mold spore, mite (e.g., Der fII) body, and mite feces).

It should be noted that, for example a cedar pollen allergy is caused by extraneous cedar pollen attached to a mucous membrane of nose, eye or throat. To be precise, pollen itself is not an antigen, but a pollen allergy allergen Cry j1 present on the surface of the pollen, or a pollen allergy allergen Cry j2 present inside the pollen, are allergens. The allergen inactivating agent of the present invention reduces the antigenicity of these allergens.

Preparative Example of Chlorine Dioxide Solution

The allergen inactivating agent of the present invention includes dissolved chlorine dioxide (e.g., chlorine dioxide solution) as an active ingredient. It is preferable that a chlorite and a pH adjuster (e.g., an acid or a salt thereof having a buffering property) are added, in order to improve the preservation stability.

For the chlorite, for example, salts of alkali metal chlorite and salts of alkali earth metal chlorite can be mentioned. Examples of the salt of alkali metal chlorite include sodium chlorite, potassium chlorite and lithium chlorite. Examples of the salt of alkali earth metal chlorite include calcium chlorite, magnesium chlorite and barium chlorite.

Especially, not only from the viewpoint of availability, but also from the viewpoint of long-term (e.g., excellent) preservation stability of dissolved chlorine dioxide, sodium chlorite and potassium chlorite are preferable, and sodium chlorite is most preferable.

For the pH adjuster, an acid (e.g., inorganic acid and organic acid) or a salt thereof, having a buffering property which gives a pH of 2.5 to 6.8 as a 5% aqueous solution at 25° C., is preferable. When the pH is below 2.5 or above 6.8, the preservation stability of the dissolved chlorine dioxide is reduced, and a change in a liquid property (e.g., pH) of the chlorine dioxide solution during preservation becomes large. It is preferable to use an acid (e.g., inorganic acid and organic acid) or a salt thereof having a buffering property which gives a pH of 3.5 to 6.0 as a 5% aqueous solution at 25° C., and it is more preferable to use one giving a pH of 4.0 to 5.5.

Examples of the pH adjuster include phosphoric acid, boric acid, metaphosphoric acid, pyrophosphoric acid, sulfamic acid and acetic acid. Examples of the salt thereof include sodium dihydrogenphosphate and a mixture of sodium dihydrogenphosphate with disodium hydrogenphosphate.

Especially, phosphoric acid or a salt thereof is preferred, and sodium dihydrogenphosphate is more preferred, since the preservation stability is excellent and a change in the liquid property (e.g., pH) during preservation is suppressed to a minimum, leading to excellent action of reducing the antigenicity.

It should be noted that one kind of the pH adjuster may be used alone or two or more kinds thereof may be used in combination. The final pure chlorine dioxide solution has a pH of preferably 4.5 to 6.5, more preferably 5.5 to 6.0, since the preservation stability is excellent for a long term, and a pH change during preservation is suppressed.

It should also be noted that, the expression "pure chlorine dioxide solution" herein means that chlorine dioxide is present in a form of chlorine dioxide gas.

For the concentration of chlorine dioxide that reduces the antigenicity of the allergen, from 0.05 ppm to 1 ppm is preferable, from 0.1 ppm to 1 ppm is more preferable, and from 0.1 ppm to 0.6 ppm is still more preferable. When the concentration is above 1 ppm, a safety problem may occur, and when below 0.05 ppm, effects as expected may not be obtained.

Example of the forms of application include a nasal lavage fluid, collyrium, eye-drop, nasal solution (e.g., nasal spray), spray for throat, liniment for throat, and gargle. Specifically, it is possible to prevent allergic manifestations and alleviate allergic symptoms, by inactivating the allergen with the dissolved chlorine dioxide and washing down the allergen with the agent as wash solution, and thus by suppressing the amount of the allergen to a threshold or less. For example, an appropriate amount of the dissolved chlorine dioxide (e.g., aqueous solution of chlorine dioxide) having the concentration of from 0.1 ppm to 0.6 ppm may be applied externally as the nasal lavage fluid, collyrium, gargle or the like, 3 to 6 times per day.

Chlorine dioxide gas generated by the conventional method can be used as the allergen inactivating agent of the present invention.

Since the manifestation of allergy is often triggered by inhaling airborne allergens, the inactivating agent of the present invention can be used for the purpose of improving living environment. Specifically, allergic manifestations and allergic symptoms which may otherwise be caused in a person in such a environment can be prevented or alleviated, by spraying the dissolved chlorine dioxide solution in a form of mist inside a building or a room, or by diffusing the chlorine dioxide gas in the living environment. For spraying in a form of mist, the conventional methods can be used, and examples include a method using an atomizing device utilizing ultrasonic, a method using a centrifugal atomizing device, e.g., a method of atomization using a centrifugal force of a motor, a method using an aerosol propellant, and a method using air fog, e.g., a method for spraying the solution together with compressed air, in which atomization is made using a compressor.

When the allergen inactivating agent of the present invention includes the chlorite and the pH adjuster (e.g., an inorganic acid or a salt thereof having a buffering property), excellent preservation stability can be obtained. For example, the dissolved chlorine dioxide concentration can be maintained constant for a long term, and even when chlorine dioxide is continuously released by portions as gas from the inactivating agent or even when chlorine dioxide gas is aggressively kept released, the chlorine dioxide concentration in the inactivating agent can be held in an approximately constant range.

The expression "continuously released by portions as gas" herein means that, for example, during transportation or preservation, even though a lid of a container is closed, chlorine dioxide dissipates as gas in the course of nature, and the expression "chlorine dioxide gas is aggressively kept released" herein means that gas dissolved in the solution is diffused in an atmosphere with an expectation of obtaining action of reducing the antigenicity of the allergen.

When phosphoric acid or a salt thereof is used as an inorganic acid or a salt thereof having a buffering property, as compared with other inorganic acids or organic acids, the preservation stability is further improved (e.g., period with the preservation stability is further extended), and fluctuation or change in a liquid property (e.g., pH) over time during preservation is suppressed.

Moreover, by selecting sodium dihydrogenphosphate or the mixture of sodium dihydrogenphosphate with disodium hydrogenphosphate from among numerous inorganic acids or salts thereof, and by combining this with sodium chlorite, an excessive progression of a reaction in which sodium chlorite turns into chlorine dioxide hardly occurs. Therefore, a gas equilibration state is retained by replenishing chlorite ion from sodium chlorite that compensates only chlorine dioxide that is lost by natural decomposition or that dissipates from a lid portion or walls of the container. As described above, the present invention is suitable in that unnecessary consumption of sodium chlorite is suppressed and sodium chlorite is efficiently consumed, leading to further improvement in the preservation stability (e.g., period with the preservation stability is further extended), and to further suppression of fluctuation or change in the chlorine dioxide concentration over time during preservation (e.g., both the decrease and increase in the concentration can be suppressed).

In addition, a mechanism of the inactivating agent for replenishing chlorine dioxide from sodium chlorite for a long term is exerted even in a space or on a subject, to which the inactivating agent is applied, sprayed or diffused. This provides an excellent sustained effect, i.e. lasting allergen inactivation action or action of reducing the antigenicity after application, spraying or diffusion of the inactivating agent, further providing a great merit upon its use.

EXAMPLES

Hereinbelow, an example of the present invention will be described, but the present invention should not be limited to the following example.

Preparation Example 1

An aqueous solution of chlorine dioxide was obtained by a conventional method. Specifically, chlorine dioxide gas generated using an acid is extracted and dissolved in water (by a bubbling method, for example), to thereby obtain 1,000 ml of the aqueous solution of chlorine dioxide.

Preparation Example

In the following manner, an aqueous solution of chlorine dioxide was prepared. Specifically, to 250 ml of water in which 2,000 ppm of chlorine dioxide gas had been dissolved were added 680 ml of water and 80 ml of a 25% solution of sodium chlorite, and stirred. Subsequently, to the solution was added sodium dihydrogenphosphate in such an amount that the pH of the solution became 5.5 to 6.0 and stirred, to thereby obtain 1,000 ml of an aqueous solution of chlorine dioxide including chlorine dioxide gas dissolved therein, sodium chlorite, and sodium dihydrogenphosphate.

Experiment on Cedar Pollen Allergen (Cry j1)

The aqueous solutions of chlorine dioxide each obtained in Preparative Examples 1 and 2 were diluted by a conventional method to various concentrations (for Preparative Example 1, five different concentrations, 0.1 ppm, 0.5 ppm, 1 ppm, 5 ppm, and 10 ppm, and for Preparative Example 2, five different concentrations, 0.1 ppm, 0.5 ppm, 1 ppm, 5 ppm, and 10 ppm), and using these dilutions, effects on Cry j1, which is one type of the cedar pollen allergen, were examined. Distilled water was used as a control.

Experiment Description and Result

In order to establish a procedure of quantification of cedar pollen antigen, ELISA (enzyme-linked immunosorbent assay) was used to create a standard curve for quantification of cedar pollen Cry j1 available from Hayashibara Biochemical Labs., Inc. See FIG. 1. As shown in FIG. 1, there was a linear relationship (R=0.999) between the Cry j1 concentration and the absorbance.

Next, the purified Cry j1 was reacted with each of various concentrations of the aqueous solutions of chlorine dioxide obtained in Preparative Examples 1 and 2 for 10 minutes, and for each case measurement was made using ELISA. As a result, in both cases of the aqueous solution of chlorine dioxide obtained in Preparative Example 1 and the aqueous solution of chlorine dioxide obtained in Preparative Example 2 (concentration: 0.1 ppm), the antigenicity of Cry j1 was significantly reduced, as compared with the case of distilled water as a control. In addition, Cry j1 was reacted with each of aqueous solutions of chlorine dioxide obtained in Preparative Examples 1 and 2 (concentration: 0.5 ppm), and change in the antigenicity of Cry j1 over time was examined. As a result, in both cases of the aqueous solution of chlorine dioxide obtained in Preparative Example 1 and the aqueous solution of chlorine dioxide obtained in Preparative Example 2 (concentration: 0.5 ppm), the antigenicity of Cry j1 was reduced below the detection limit, 15 seconds after the addition. On the other hand, the effect exerted by tap water was very low. The details will be described below.

Experimental Method and Result

In order to examine efficacy of chlorine dioxide on Cry j1, a quantification of Cry j1 was established by an enzyme-linked immunosorbent assay using an anti-Cry j1 mouse monoclonal antibody No. 013 (anti-Cry j1 mAb 013 available from Hayashibara Biochemical Labs., Inc.) and an enzyme-labeled anti-Cry j1 mouse monoclonal antibody No. 053 (Peroxidase conjugated anti-Cry j1 mAb053 available from Hayashibara Biochemical Labs., Inc.).

First, the antibody (anti-Cry j1 mAb 013) for a solid phase was diluted with PBS to 10 μg/ml, and 100 μl of the dilution was added to each well of a 96-well microplate available from Nunc Immuno Plate, Maxisorp F96 CERT, Nunc Co., and the plate was allowed to stand still at room temperature for 2.5±0.5 hours. After that time period, the solid phase antibody solution was removed, 250 μl of 0.1% BSA-containing PBS was added to each well, and the plate was allowed to stand still at 4° C. overnight. The PBS containing 0.1% BSA (SIGMA) was removed from the plate, 100 μl of the prepared standard solution and 100 μl of a test liquid were added to each well, and the plate was allowed to stand still at room temperature for 1.5±0.5 hours. After that time period, the standard solution and the test liquid were removed from the plate, and each well was washed with 250 μl of Tween 20-containing PBS 3 times. Subsequently, the enzyme-labeled antibody (peroxidase conjugated anti-Cry j1 mAb 053) was diluted 1,000 fold with 0.1% BSA-containing PBS, 100 μl of the dilution was added to each well, and the plate was allowed to stand still at room temperature for 2.0±0.5 hours. The enzyme-labeled antibody was removed from the plate, and each well was washed with Tween 20-containing PBS 3 times. A substrate solution was prepared by adding 5 mg of o-phenylenediamine and 10 μL of 30% hydrogen peroxide water to 10 ml of a 0.1 M citric acid-phosphoric acid buffer solution having a pH of 5.0 (0.1 M citric acid-phosphoric acid buffer solution had been prepared by adding water to 7.0 g of citric acid monohydrate and 23.9 g of disodium hydrogenphosphate dodecahydrate to obtain a solution, adjusting its pH to 5.0 with HCL, adding water to the total volume of 1,000 ml, and sterilizing the solution by filtration), 100 μl thereof was added to each well, and the plate was allowed to stand still for 3 to 5 minutes. To each well was added 100 μl of 2N sulfuric acid to terminate the enzymatic reaction, and within 30 minutes after the addition of sulfuric acid, an absorbance of A492 was measured using a plate reader.

Each of the aqueous solutions of chlorine dioxide obtained in Preparative Examples 1 and 2 having various concentrations was reacted with the purified Cry j1 (Japanese cedar pollen allergen Cry j1, purified) having the final concentration of 5 μg/ml. To Cry j1 was added each of the aqueous solutions of chlorine dioxide obtained in Preparative Example 1 having concentrations from 0.1 ppm to 10 ppm, the aqueous solutions of chlorine dioxide obtained in Preparative Example 2 having concentrations of 0.1 ppm to 10 ppm, and tap water from four cities (Suita City, Osaka City, Toyonaka City, and Kyoto City), and 10 minutes later, an aqueous solution of 0.1M sodium thiosulfate was added to each mixture to neutralize the mixture. Each of the reaction solutions was diluted with 0.1% BSA-containing PBS to approximately 16.0 ng/ml, and the resultant dilution was used as a test liquid. Distilled water was used as a control.

Figure 2:
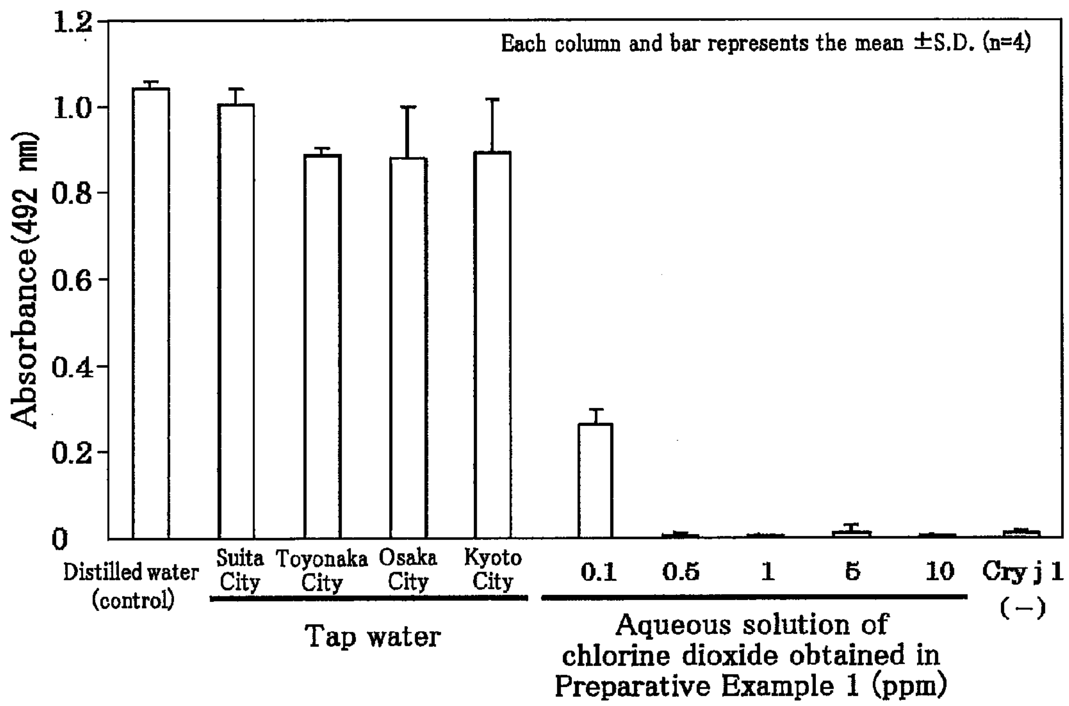
FIG. 2 is a graph showing effect of dissolved chlorine dioxide on Cry j1 antigenicity.
Figure 3:
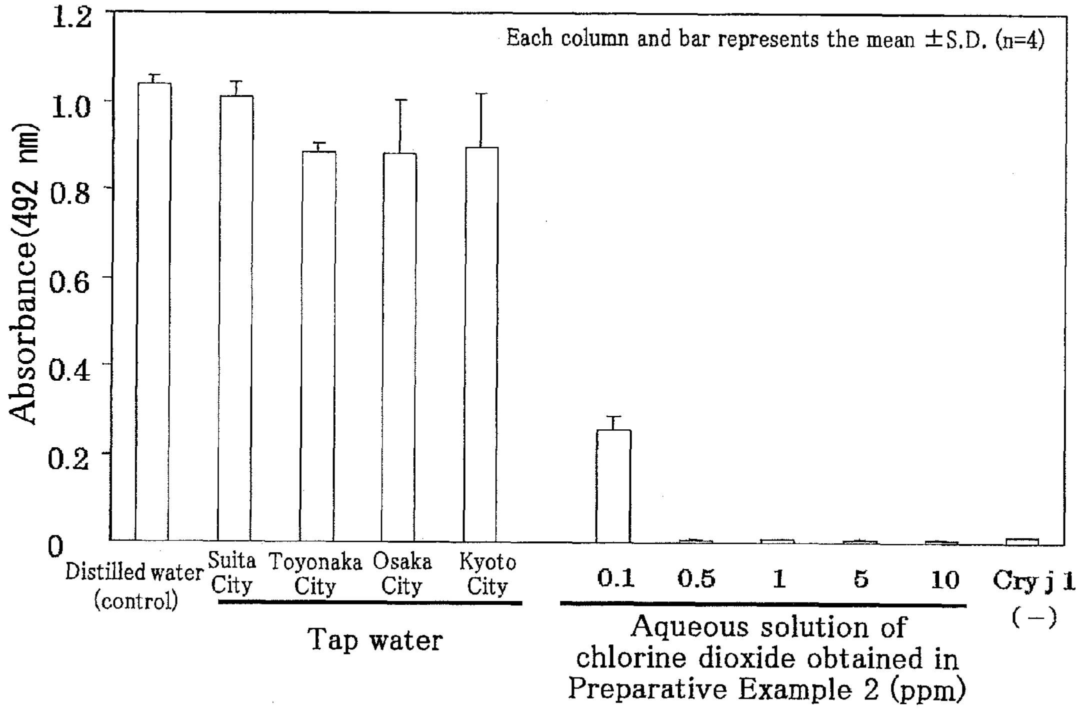
FIG. 3 is a graph showing effect of dissolved chlorine dioxide on Cry j1 antigenicity.

The results are shown in FIGS. 2 and 3. FIG. 2 is a graph showing effect of dissolved chlorine dioxide on Cry j1 antigenicity, in a case where an aqueous solution of chlorine dioxide obtained in Preparative Example 1 was used. FIG. 3 is a graph showing effect of dissolved chlorine dioxide on Cry j1 antigenicity, in a case where an aqueous solution of chlorine dioxide obtained in Preparative Example 2 was used. As is apparent from these figures, in the case where 5 μg/ml of Cry j1 was reacted with each of the aqueous solutions of chlorine dioxide obtained in Preparative Examples 1 and 2 having concentrations from 0.1 ppm to 10 ppm, the addition of 0.5 ppm of the aqueous solution of chlorine dioxide remarkably reduced the antigenicity of Cry j1, as compared with the case of distilled water as a control. The addition of 0.1 ppm of the aqueous solutions of chlorine dioxide obtained in Preparative Examples 1 and 2 significantly reduced the antigenicity. On the other hand, the effect exerted by tap water from four cities was very low.

In addition, effect in terms of time of the aqueous solution of chlorine dioxide on the antigenicity of Cry j1 was examined. Five μg/ml of Cry j1 was reacted with each of the aqueous solutions of chlorine dioxide obtained in Preparative Examples 1 and 2 (concentration: 0.5 ppm) and tap water from four cities (Suita City, Osaka City, Toyonaka City, and Kyoto City), the reaction solution was diluted to 16.0 ng/ml, and the resultant dilution was used as a test liquid. Distilled water was used as a control.

Figure 4:
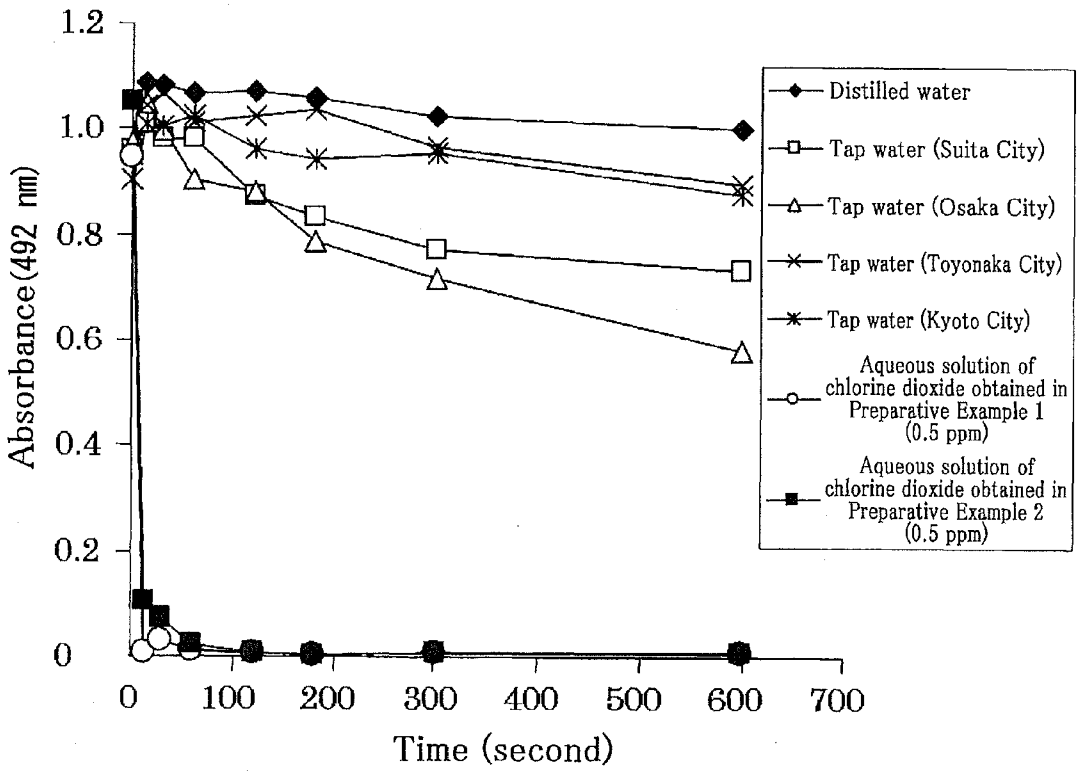
FIG. 4 is a graph showing change over time in effect of dissolved chlorine dioxide in reducing (inactivating) Cry j1 antigenicity.

As a result, as shown in FIG. 4, in both of the aqueous solution of chlorine dioxide obtained in Preparative Example 1 and the aqueous solution of chlorine dioxide obtained in Preparative Example 2, the antigenicity of Cry j1 was remarkably reduced immediately after the addition, as compared with distilled water. In the water quality management target criterion in accordance with Water Supply Law, it is defined that the chlorine dioxide concentration should be 0.6 mg/L (ppm) or less, and therefore if efficacy of chlorine dioxide is shown with a value within this range, it is considered that the equivalent level of safety to that of tap water is obtained. On the other hand, if the recent ordinary tap water itself is capable of reducing the antigenicity to the same extent as 0.5 ppm of the aqueous solution of chlorine dioxide does, it is considered that chlorine dioxide has no usefulness. Accordingly, chlorinated tap water from four cities (Suita City, Osaka City, Toyonaka City, and Kyoto City) was examined in substantially the same manner. However, the effects thereof were very low.

From the results above, it was elucidated that 0.1 ppm of the aqueous solution of chlorine dioxide satisfactorily reduces the antigenicity of Cry j1, and 0.5 ppm of the aqueous solution of chlorine dioxide instantly reduces the antigenicity of Cry j1, and that such an effect cannot be obtained with water.

Experiment on Mite Allergen (Der fII)

Following the cedar pollen allergen, an effect of the aqueous solution of chlorine dioxide on Der Fii available from Asahi Breweries, Ltd., which is one of mite allergens, was examined.

Experiment Description and Result

Figure 5:
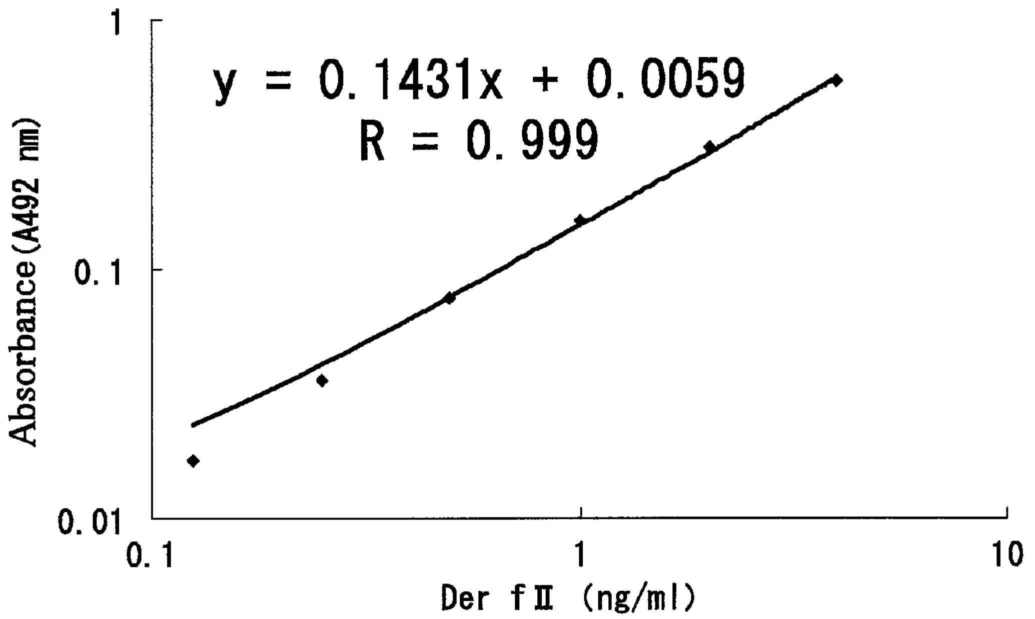
FIG. 5 is a graph showing a standard curve for Der fII.

In order to establish a procedure of quantification of mite antigen, ELISA (enzyme-linked immunosorbent assay) was used to create a standard curve for quantification of Der fII. There was a linear relationship (R=0.999) between the Der fII concentration and the absorbance (FIG. 5). Next, the purified Der fII was reacted with each of various concentrations of the aqueous solutions of chlorine dioxide for 10 minutes, and for each case measurement was made using ELISA. As a result, the addition of the aqueous solution of chlorine dioxide significantly reduced the antigenicity of Der fII, as compared with the case of distilled water as a control. The details will be described below.

Experimental Method and Result

In order to examine efficacy of chlorine dioxide on Der fII, a quantification of Der fII was established by an enzyme-linked immunosorbent assay using an anti-Der fII mouse monoclonal antibody No. 15E11 available from Asahi Breweries, Ltd. and a HRP-labeled anti-Der fII mouse monoclonal antibody No. 13A4 available from Asahi Breweries, Ltd.

First, the antibody (anti-Der fII monoclonal antibody 15E11) for a solid phase was diluted with PBS to 4 ng/ml, and 50 μl of the dilution was added to each well of a 96-well microplate available from Nunc Immuno Plate, Maxisorp F96 CERT, Nunc Co., and the plate was allowed to stand still at room temperature for 2.0±0.5 hours. After that time period, the solid phase antibody solution was removed, and each well was washed with 200 μl of PBS 3 times. Subsequently, 200 μl of PBS containing 0.1% BSA (SIGMA) was added to each well, and the plate was allowed to stand still at 4° C. overnight. The PBS containing 0.1% BSA was removed from the plate, 50 μl of the prepared standard solution and 50 μl of a test liquid were added to each well, and the plate was allowed to stand still at room temperature for 2.0±0.5 hours. After that time period, the standard solution and the test liquid were removed from the plate, and each well was washed with 200 μl of Tween 20-containing PBS 3 times. Subsequently, the enzyme-labeled antibody (HRP-labeled anti-Der fII monoclonal antibody 13A4) was diluted with Tween 20-containing PBS to 0.5 μg/ml, 50 μl of the dilution was added to each well, and the plate was allowed to stand still at room temperature for 2.0±0.5 hours. The enzyme-labeled antibody was removed from the plate, and each well was washed with Tween 20-containing PBS 3 times. A substrate solution was prepared by adding 5 mg of o-phenylenediamine and 10 μL of 30% hydrogen peroxide water to 10 ml of a 0.1 M citric acid-phosphoric acid buffer solution having a pH of 5.0 (0.1 M citric acid-phosphoric acid buffer solution had been prepared by adding water to 7.0 g of citric acid monohydrate and 23.9 g of disodium hydrogenphosphate dodecahydrate to obtain a solution, adjusting its pH to 5.0 with HCL, adding water to the total volume of 1,000 ml, and sterilizing the solution by filtration), 100 μl thereof was added to each well, and the plate was allowed to stand still for 3 to 5 minutes. To each well was added 100 μl of 2N sulfuric acid to terminate the enzymatic reaction, and within 30 minutes after the addition of sulfuric acid, an absorbance of A492 was measured using a plate reader.

Each of the aqueous solutions of chlorine dioxide having various concentrations and tap water was reacted with the purified mite antigen Der fII having the final concentration of 5 μg/ml. To Der fII was added each of the aqueous solutions of chlorine dioxide having concentrations from 40 ppm to 0.5 ppm, and 10 minutes later, an aqueous solution of 1 M sodium thiosulfate was added to each mixture to neutralize the mixture. Each of the reaction solutions was diluted with Tween 20-containing PBS to approximately 4.0 ng/ml, and the resultant dilution was used as a test liquid. As a control, distilled water in an equal amount to that of the aqueous solution of chlorine dioxide was added.

Figure 6:
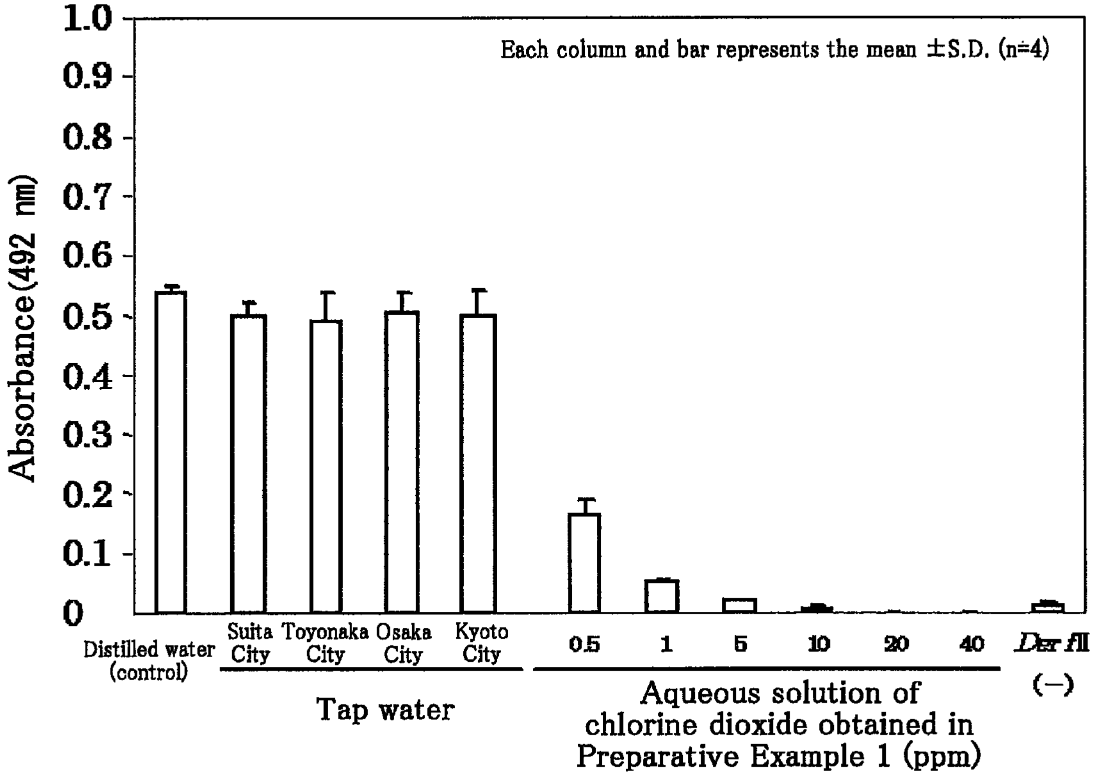
FIG. 6 is a graph showing effect of dissolved chlorine dioxide on Der fII antigenicity.
Figure 7:
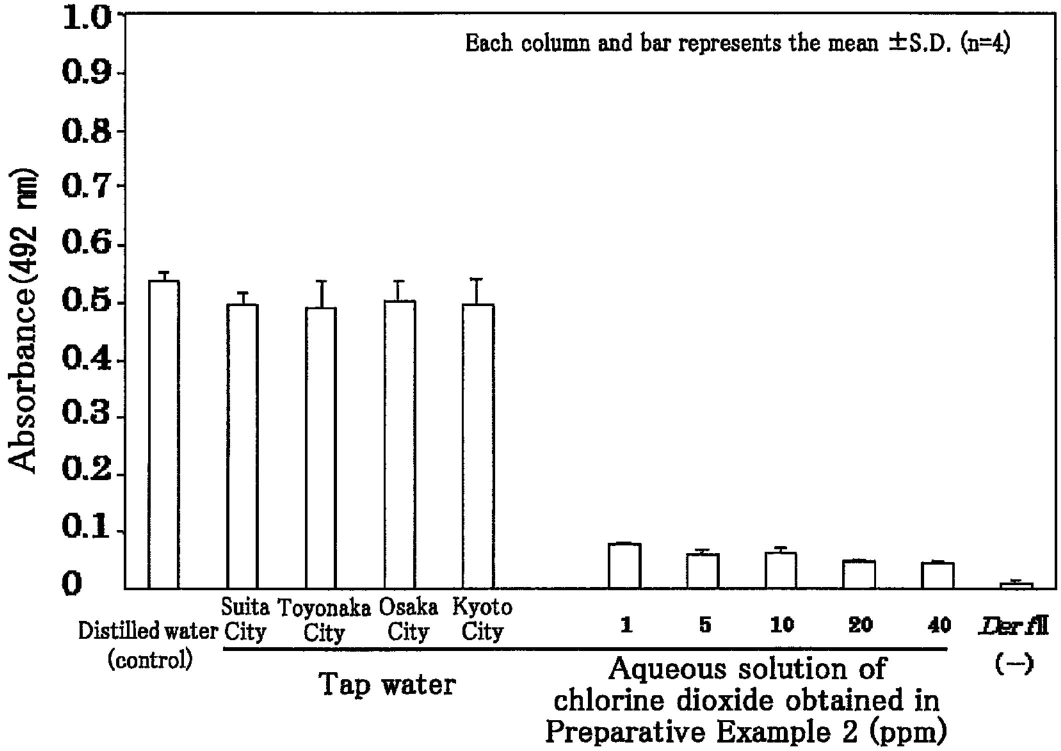
FIG. 7 is a graph showing effect of dissolved chlorine dioxide on Der fII antigenicity.

In the case where 5 μg/ml of Der fII was reacted with each of the aqueous solutions of chlorine dioxide obtained in Preparative Example 1 having concentrations from 40 ppm to 0.5 ppm, the addition of 1 ppm of the aqueous solution of chlorine dioxide remarkably reduced the antigenicity of Der fII, as compared with the case of distilled water as a control. The addition of 0.5 ppm of the aqueous solution of chlorine dioxide also reduced the antigenicity See FIG. 6. FIG. 6 is a graph showing effect of dissolved chlorine dioxide on Der fII antigenicity, in a case where an aqueous solution of chlorine dioxide obtained in Preparative Example 1 was used. Next, in the case where 5 μg/ml of Der III was reacted with each of the aqueous solutions of chlorine dioxide obtained in Preparative Example 2 having concentrations from 40 ppm to 0.5 ppm, the addition of 0.5 ppm of the aqueous solution of chlorine dioxide reduced the antigenicity of Der fII, as compared with the case of distilled water as a control See FIG. 7. FIG. 7 is a graph showing effect of dissolved chlorine dioxide on Der fII antigenicity, in a case where an aqueous solution of chlorine dioxide obtained in Preparative Example 2 was used.

From the results above, it was elucidated that the aqueous solution of chlorine dioxide satisfactorily reduces the antigenicity of Der fII.

Experiment on Effect of Chlorine Dioxide Gas in Reducing Antigenicity

Instead of the aqueous solution of chlorine dioxide, chlorine dioxide gas was examined with respect to an effect thereof in reducing the antigenicity of Cry j1.

Experiment Description and Result

The purified Cry j1 which had been freeze-dried was reacted with chlorine dioxide gas having an average concentration of 0.08 ppm for 24 hours, and measurement was made using ELISA. As a result, 0.08 ppm of chlorine dioxide gas reduced the antigenicity of Cry j1, as compared with the case of air as a control. In addition, when humidity was increased, the antigenicity was further reduced. The details will be described below.

Experimental Method and Result

In order to examine effect of the chlorine dioxide gas on the freeze-dried Cry j1, 10 ml of the purified Cry j1 adjusted with PBS to the concentration of 10 μg/ml was placed in a 0.2-μL tube, frozen at −30° C., and freeze-dried overnight using a suction desiccator.

The humidity was controlled using agar, and the generated chlorine dioxide solution was introduced using a syringe into a 100 L-Tedlar bag, so that the concentration therein becomes 0.1 ppm, and air inside the bag was agitated using a crisscross rotor wherein outer diameter of 60 mm×height of 17 mm. Likewise, a bag into which distilled water was introduced was used as a control. The bag was left in an environment of 24° C., and the chlorine dioxide gas concentration inside the bag was measured using a chlorine dioxide gas measuring instrument (Model 4330-SP, Interscan Corporation; measurement range 0 to 1,000 ppb), and when the value was below 0.1 ppm, the generated chlorine dioxide solution was further added to make adjustment.

Twenty four hours later, the tube containing Cry j1 was removed from the bag, to which 100 μl of PBS was added to obtain a solution of 1 μg/mL. The solution was diluted with 0.1% BSA-containing PBS to approximately 32.0 ng/ml, and measurement was made using ELISA.

Figure 8:
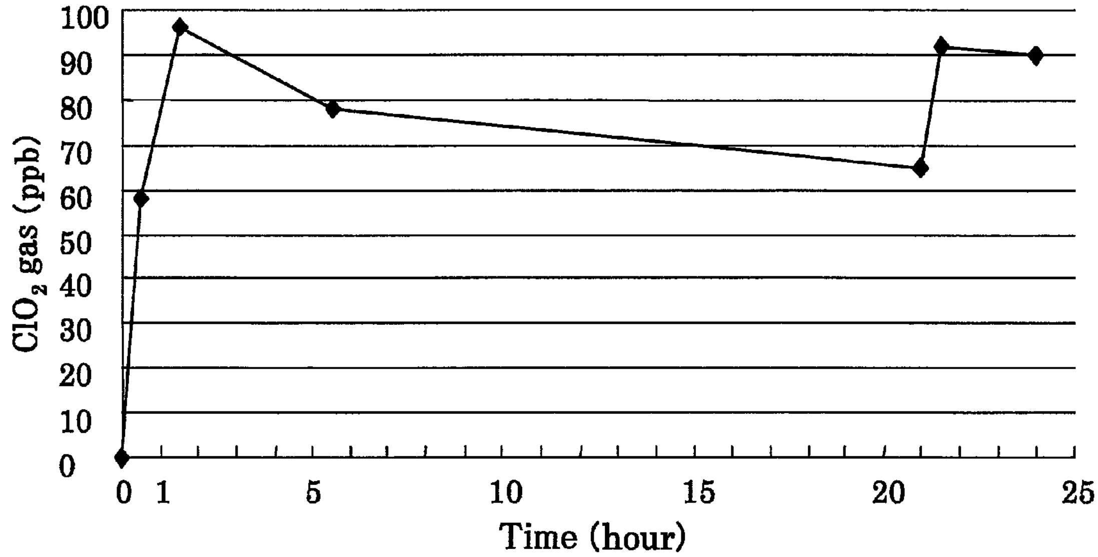
FIG. 8 is a graph showing chlorine dioxide gas concentration in a 100 L-Tedlar bag during experiment.
Figure 9:
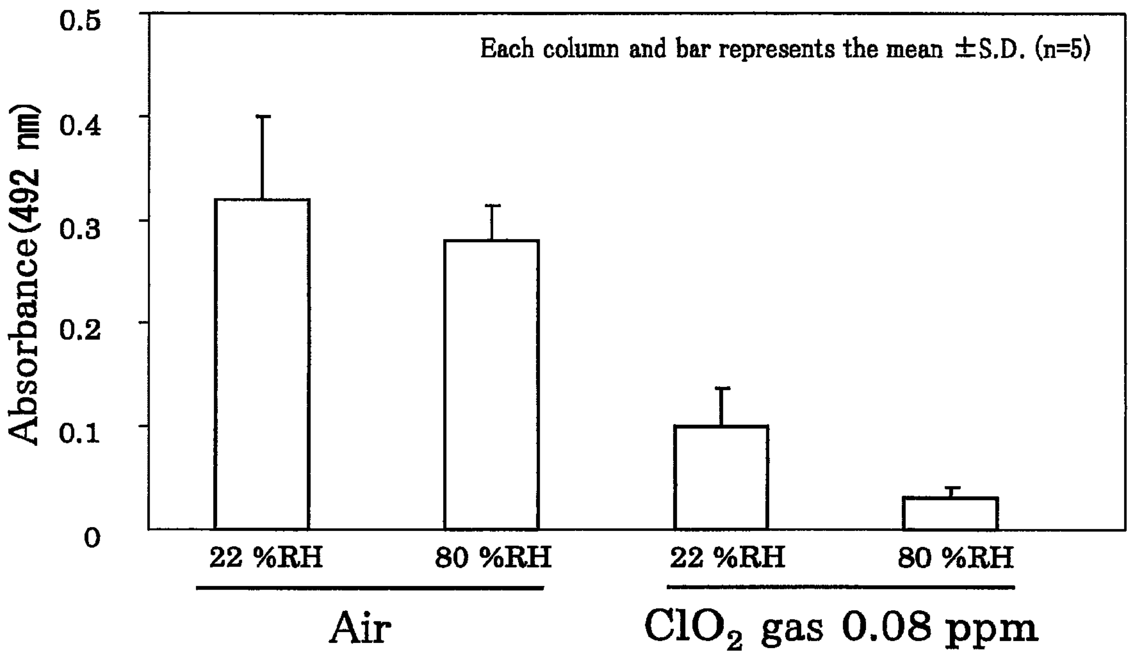
FIG. 9 is a graph showing effect of chlorine dioxide gas on freeze-dried Cry j1 antigenicity.

The chlorine dioxide gas concentration in the 100 L-Tedlar bag was 80 ppb on average (FIG. 8). When the freeze-dried Cry j1 was reacted with 0.1 ppm of chlorine dioxide gas for 24 hours, the antigenicity of Cry j1 was remarkably reduced, as compared with the case of air as a control (FIG. 9). In addition, when relative humidity was higher, the antigenicity was reduced to a larger degree.

Experiment on Effect of Chlorine Dioxide Gas in Reducing Antigenicity

Instead of the aqueous solution of chlorine dioxide, chlorine dioxide gas was examined with respect to an effect thereof in reducing the antigenicity of Der fII.

Experiment Description and Result

The purified Der fII which had been freeze-dried was reacted with chlorine dioxide gas having a concentration of 0.1 ppm for 24 hours, and measurement was made using ELISA. As a result, 0.1 ppm of chlorine dioxide gas reduced the antigenicity of Der fII, as compared with the case of air as a control. In addition, when humidity was increased, the antigenicity was further reduced. The details will be described below.

Experimental Method and Result

In order to examine effect of the chlorine dioxide gas on the freeze-dried Der fII, 10 μl of the purified Der fII adjusted with PBS to the concentration of 10 μg/ml was placed in a 0.2-mL tube, frozen at −30° C., and freeze-dried overnight using a suction desiccator.

The humidity was controlled by a saturated salt method. Inside a Futon bag, a Tupperware containing salt or water therein was placed so as to obtain a target humidity, and next day, inside the bag, a 100 L-Tedlar bag containing the freeze-dried Der fII and a hygrometer was placed. A Tedlar bag into which chlorine dioxide was introduced was light-shielded with aluminum foil. A dense chlorine dioxide gas had been generated in the 5 L-Tedlar bag in advance, and next day, the dense chlorine dioxide gas was introduced using a syringe into the 100 L-Tedlar bag, so that the concentration therein becomes 0.1 ppm, and air inside the bag was agitated using a crisscross rotor wherein outer diameter of 60 mm×height of 17 mm. Likewise, a bag into which air was introduced was used as a control. The bag was left in an environment of 24° C., and the chlorine dioxide gas concentration inside bag was measured using a chlorine dioxide detector tube (No. 23M having a measurement range of 0.1 to 10 ppm, No. 23L having a measurement range of 0.025 to 1.2 ppm, GASTEC Corporation), and when the value was below 0.1 ppm, the generated chlorine dioxide gas was further added to make adjustment.

Twenty four hours later, the tube containing Der fII was removed from the bag, to which 100 μl of PBS was added to obtain a solution of 1 μg/mL. The solution was diluted with T-PBS to approximately 8 ng/ml, and measurement was made using ELISA.

Figure 10:
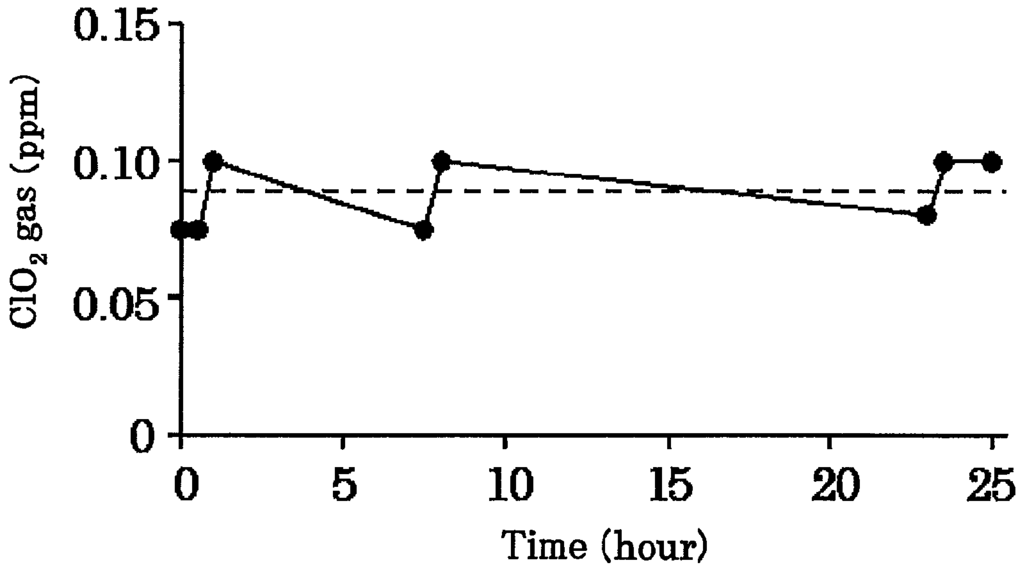
FIG. 10 is a graph showing chlorine dioxide gas concentration in a 100 L-Tedlar bag during experiment.
Figure 11:
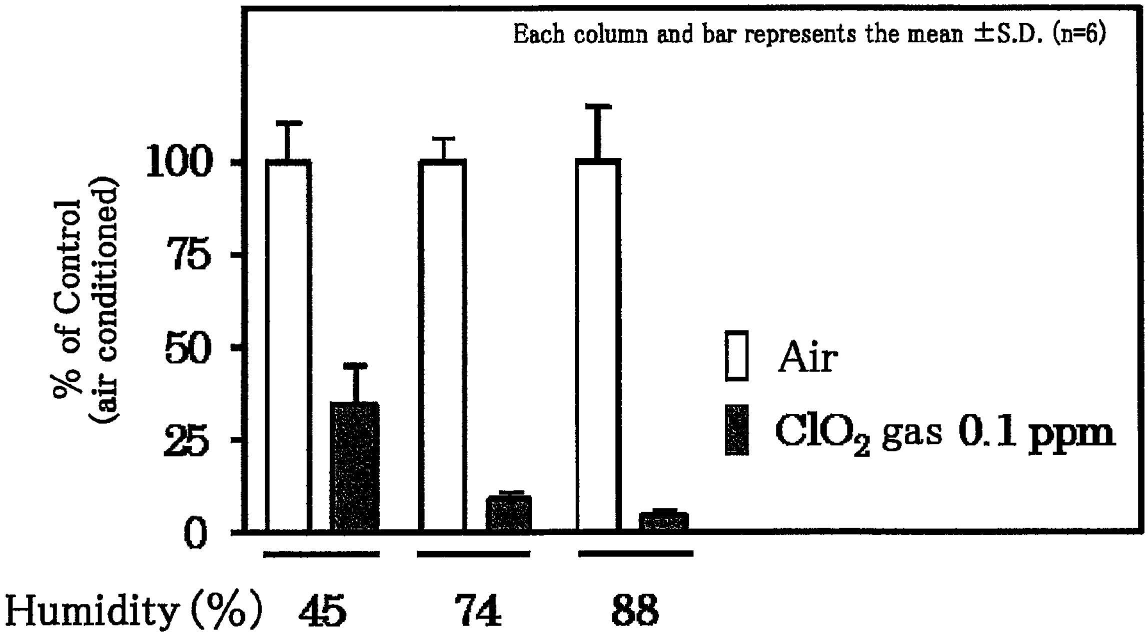
FIG. 11 is a graph showing effect of chlorine dioxide gas on freeze-dried Der fII antigenicity.

The chlorine dioxide gas concentration in the 100 L-Tedlar bag was 0.09 ppm on average (FIG. 10). When the freeze-dried Der fII was reacted with 0.1 ppm of chlorine dioxide gas for 24 hours, the antigenicity of Der fII was remarkably reduced, as compared with the case of air as a control (FIG. 11). In addition, when relative humidity was higher, the antigenicity was reduced to a larger degree.

Experiment on Fungal Allergen (Alt a 1)

Following the cedar pollen allergen (Cry j1) and the mite allergen (Der fII), an effect of the aqueous solution of chlorine dioxide on Alt a 1, which is one of fungal allergens, was examined.

Experiment Description and Result

Figure 12:
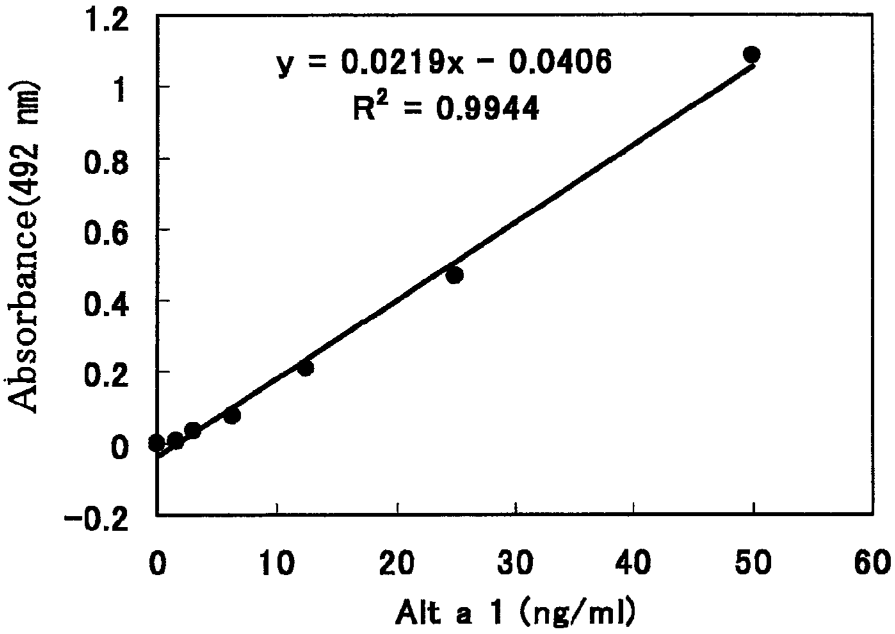
FIG. 12 is a graph showing a standard curve for Alt a 1.

In order to establish a procedure of quantification of fungal antigen, ELISA (enzyme-linked immunosorbent assay) was used to create a standard curve for quantification of Alt a 1 (FIG. 12). As shown in FIG. 12, there was a linear relationship ($R^2$=0.994) between the Alt a 1 concentration and the absorbance. Next, the purified Alt a 1 was reacted with each of various concentrations of the aqueous solutions of chlorine dioxide for 10 minutes, and for each case measurement was made using ELISA. As a result, the addition of the aqueous solution of chlorine dioxide significantly reduced the antigenicity of Alt a 1, as compared with the case of distilled water as a control. The details will be described below.

Experimental Method and Results

In order to examine efficacy of chlorine dioxide on Alt a 1 available from INDOOR biotechnologies LTD, a quantification of Alt a 1 was established by an enzyme-linked immunosorbent assay using an anti-Alt a 1 mouse monoclonal antibody 121 available from INDOOR biotechnologies LTD and a biotinylated anti-Alt a 1 mouse monoclonal antibody 121 available from INDOOR biotechnologies LTD.

First, the antibody (anti-Alt a 1 mouse monoclonal antibody 121) for a solid phase was diluted with 50 mM carbonate-bicarbonate (pH 9.6) to 2 μg/ml, and 100 μl of the dilution was added to each well of a 96-well microplate available from Nunc Immuno Plate, Maxisorp F96 CERT, Nunc Co. and, the plate was allowed to stand still at 4° C. overnight. After the time period, the solid phase antibody solution was removed, and each well was washed with 250 μl of 0.05% T-PBS 3 times. Subsequently, 100 μl of T-PBS containing 1% BSA (SIGMA) was added to each well, and the plate was allowed to stand still for 30 minutes. Next, T-PBS containing 1% BSA was removed from the plate, and each well was washed with 250 μl of 0.05% T-PBS 3 times. One hundred μl of the prepared standard solution and 100 μl of a test liquid were added to each well, and the plate was allowed to stand still at room temperature for 1 hour. After that time period, the standard solution and the test liquid were removed from the plate, and each well was washed with 250 μl of 0.05% T-PBS 3 times. Subsequently, the biotinylated anti-Alt a 1 mouse monoclonal antibody 121 was diluted with 1% BSA-containing T-PBS, 100 μl of the dilution was added to each well, and the plate was allowed to stand still at room temperature for 1 hour. The biotinylated antibody was removed from the plate, and each well was washed with 250 μl of 0.05% T-PBS 3 times. Next, 100 μl of streptavidin-peroxidase was added to each well, and the plate was allowed to stand still for 30 minutes. Streptavidin-peroxidase was removed from the plate, and each well was washed with 250 μl of 0.05% T-PBS 3 times. A substrate solution was prepared by adding 5 mg of o-phenylenediamine and 10 μl, of 30% hydrogen peroxide water to 10 ml of a 0.1 M citric acid-phosphoric acid buffer solution having a pH of 5.0 (0.1 M citric acid-phosphoric acid buffer solution had been prepared by adding water to 7.0 g of citric acid monohydrate and 23.9 g of disodium hydrogenphosphate dodecahydrate to obtain a solution, adjusting its pH to 5.0 with HCL, adding water to the total volume of 1,000 ml, and sterilizing the solution by filtration), 100 μl thereof was added to each well, and the plate was allowed to stand still for 3 to 5 minutes. To each well was added 100 μl of 2N sulfuric acid to terminate the enzymatic reaction, and within 30 minutes after the addition of sulfuric acid, an absorbance of A492 was measured using a plate reader.

Each of the aqueous solutions of chlorine dioxide having various concentrations and tap water were reacted with the purified fungal antigen Alt a 1 having the final concentration of 5 μg/ml. To Alt a 1 was added each of the aqueous solutions of chlorine dioxide having concentrations from 40 ppm to 0.1 ppm (0.5 ppm), and 10 minutes later, an aqueous solution of 1 M sodium thiosulfate was added to each mixture to neutralize the mixture. Each of the reaction solutions was diluted 100 fold with 1% BSA-containing T-PBS, and the resultant dilution was used as a test liquid. As a control, distilled water in an equal amount to that of the aqueous solution of chlorine dioxide was added.

Figure 13:
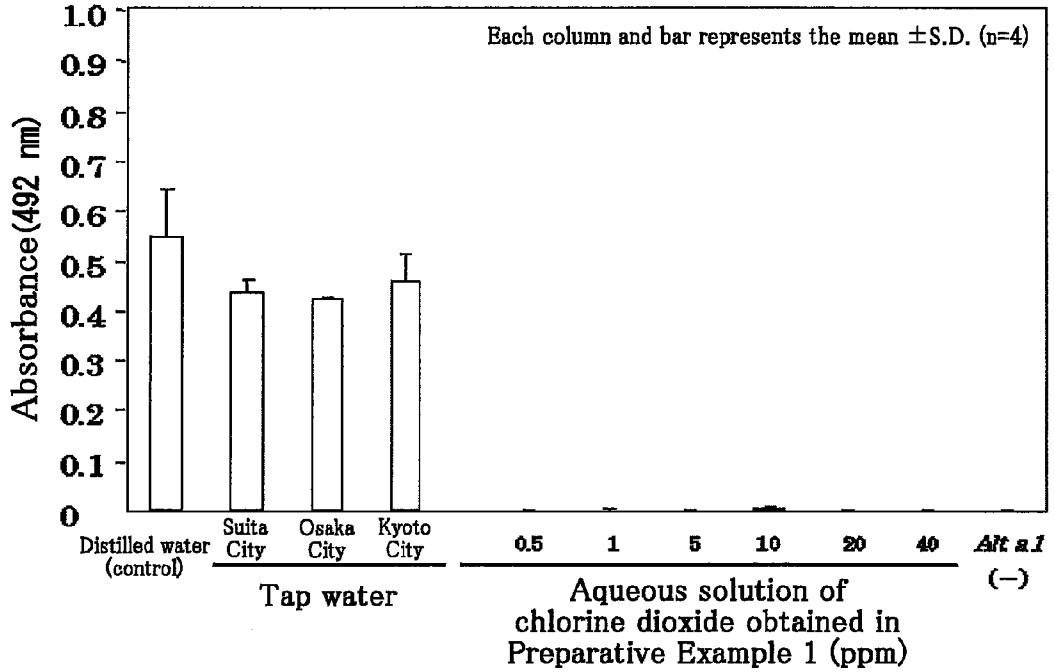
FIG. 13 is a graph showing effect of dissolved chlorine dioxide on Alt a 1 antigenicity.
Figure 14:
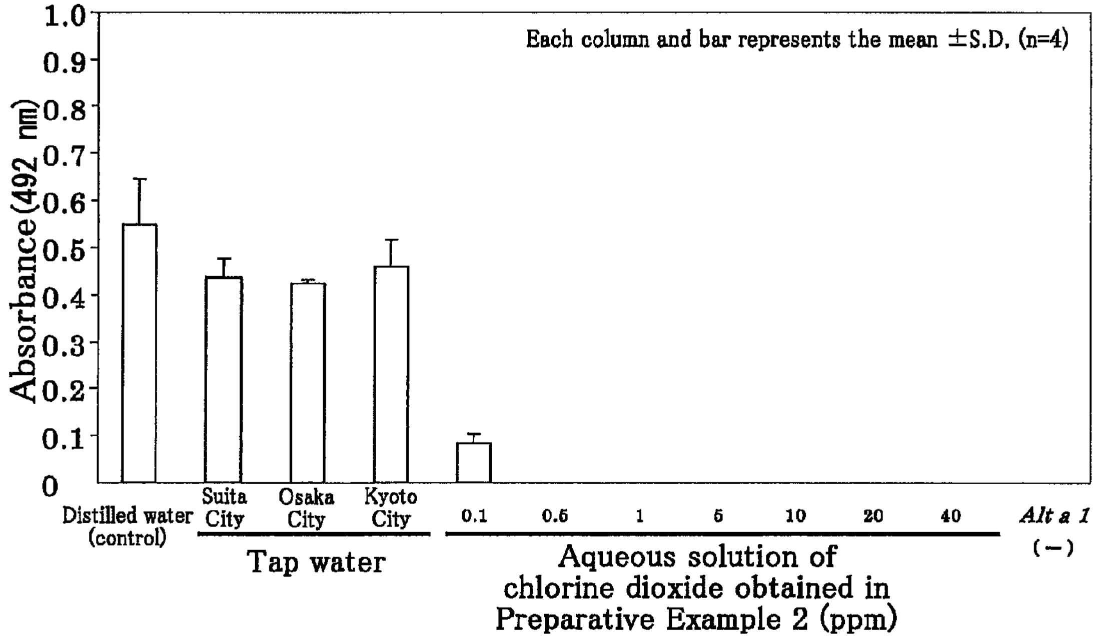
FIG. 14 is a graph showing effect of dissolved chlorine dioxide on Alt a 1 antigenicity.

In the case where 5 μg/ml of Alt a 1 was reacted with each of the aqueous solutions of chlorine dioxide obtained in Preparative Example 1 having concentrations from 40 ppm to 0.5 ppm, the addition of 0.5 ppm of the aqueous solution of chlorine dioxide reduced the antigenicity of Alt a 1 to the same level as that of the negative control, as compared with the case of distilled water as a control (FIG. 13). FIG. 13 is a graph showing effect of dissolved chlorine dioxide on Alt a 1 antigenicity, in a case where an aqueous solution of chlorine dioxide obtained in Preparative Example 1 was used. Next, in the case where 5 μg/ml of Alt a 1 was reacted with each of the aqueous solutions of chlorine dioxide obtained in Preparative Example 2 having concentrations from 40 ppm to 0.1 ppm, the addition of 0.1 ppm of the aqueous solution of chlorine dioxide reduced the antigenicity of Alt a 1, as compared with the case of distilled water as a control (FIG. 14). FIG. 14 is a graph showing effect of dissolved chlorine dioxide on Alt a 1 antigenicity, in a case where an aqueous solution of chlorine dioxide obtained in Preparative Example 2 was used.

From the results above, it was elucidated that the aqueous solution of chlorine dioxide satisfactorily reduces the antigenicity of Alt a 1.

INDUSTRIAL APPLICABILITY

The allergen inactivating agent of the present invention can be used for preventing allergic manifestations and alleviating allergic symptoms, which may otherwise be caused by pollen, house dust or the like.

The invention claimed is:

1. An allergen inactivating agent for preventing allergic manifestations or alleviating symptoms by reducing antigenicity of an allergen through contact with the allergen, the allergen inactivating agent comprising dissolved chlorine dioxide as an active ingredient, sodium chlorite, and one selected from the group consisting of sodium dihydrogenphosphate and a mixture of sodium dihydrogenphosphate with disodium hydrogenphosphate as a pH adjuster with which pH is adjusted to 4.5-6.5, wherein the chlorine dioxide is contained in such a manner that the concentration of chlorine dioxide during application for reducing the antigenicity of the allergen is from 0.1 ppm to 0.6 ppm.

2. A method for treating an environment with an allergen inactivating agent, the method comprising:

introducing the allergen inactivating agent of claim 1 into an environment in which at least one allergen is present, wherein during the introducing step, the concentration of chlorine dioxide in the allergen inactivating agent is from 0.1 ppm to 0.6 ppm.

3. The allergen inactivating agent according to claim 1, wherein the concentration of chlorine dioxide in the allergen inactivating agent is from 0.5 ppm to 0.6 ppm.

4. The method according to claim 2, wherein the concentration of chlorine dioxide in the allergen inactivating agent is from 0.5 ppm to 0.6 ppm.

* * * * *